United States Patent [19]

Kohn

[11] 3,988,471

[45] *Oct. 26, 1976

[54] INSECT CONTROL EMPLOYING CERTAIN BENZOATES

[75] Inventor: Gustave K. Kohn, Berkeley, Calif.

[73] Assignee: Chevron Research Company, San Francisco, Calif.

[ * ] Notice: The portion of the term of this patent subsequent to Feb. 18, 1992, has been disclaimed.

[22] Filed: Mar. 19, 1975

[21] Appl. No.: 559,931

Related U.S. Application Data

[63] Continuation-in-part of Ser. No. 376,871, July 5, 1973, abandoned, which is a continuation-in-part of Ser. No. 281,078, Aug. 8, 1972, Pat. No. 3,867,543.

[52] U.S. Cl. ................................ 424/301; 424/263; 424/267; 424/270; 424/272; 424/273; 424/274; 424/275; 424/283; 424/285; 424/308; 260/455 R; 260/473 R

[51] Int. Cl.² ...................... A01N 9/12; A01N 9/24
[58] Field of Search ............. 424/301, 308, DIG. 12; 260/455 R, 473 R

[56] References Cited
UNITED STATES PATENTS

| 3,136,800 | 6/1964 | Grisley | 260/455 |
| 3,557,194 | 1/1971 | Fuchsman et al. | 260/502.6 |
| 3,657,309 | 4/1972 | Dexter et al. | 260/455 |
| 3,657,322 | 4/1972 | Dexter et al. | 260/473 |

*Primary Examiner*—V. D. Turner
*Attorney, Agent, or Firm*—G. F. Magdeburger; Dix A. Newell; Raymond Owyang

[57] ABSTRACT

3,5-dialkyl-4-hydroxybenzoates, 3,5-dialkyl-4-hydroxythionobenzoates, 3,5-dialkyl-4-hydroxothiolobenzoates and 3,5-dialkyl-4-hydroxydithiobenzoates have morphogenetic hormonal mimetic activity on insects.

13 Claims, No Drawings

INSECT CONTROL EMPLOYING CERTAIN BENZOATES

RELATED APPLICATIONS

This application is a continuation-in-part of copending application Ser. No. 376,871, now abandoned filed July 5, 1973, which in turn is a continuation-in-part of Ser. No. 281,078, filed Aug. 8, 1972, now U.S. Pat. No. 3,867,543. The disclosures of Ser. Nos. 376,871 and 281,078 are incorporated herein by reference.

BACKGROUND OF THE INVENTION

1. Field of the Invention

The present invention is concerned with insecticidal compounds which have morphogenetic hormonal mimetic activity. Compounds having morphogenetic hormonal mimetic activity exert a disrupting influence upon the normal development of insects. These compounds interfere with the normal metamorphosis of the pest insects and result in the formation of individual insects of the treated species which develop abnormally and are nonviable or sterile. This ultimately leads, indirectly at least, to the destruction of the insect population.

2. Description of the Prior Art

Chemical & Engineering News, Nov. 29, 1971, pp. 9–10 (Belgian Pat. No. 767,834), discloses the use of 2,6-di-t-butyl-4-($\alpha,\alpha$-dimethylbenzyl)phenol as a mosquito larvicide.

Copending application U.S. Ser. No. 199,034 of B. R. Kennedy and L. de Vries, filed Nov. 15, 1971, now U.S. Pat. No. 3,778,370, common assignee, and Gomper, Schmidt and Kutter, Liebigs Annalin, Bd 684, 37 (1965), disclose some of the dithiobenzoates and thiolobenzoates used in the method of the present invention, e.g., methyl 3,5-di-t-butyl-4-hydroxydithiobenzoate and methyl 3,5-di-t-butyl-4-hydroxythiolobenzoate.

SUMMARY OF THE INVENTION

It has now been found that esters of 3,5-di-(branched alkyl)-4-hydroxybenzoic acids,
3,5-di-(branched alkyl)-4-hydroxythionobenzoic acids,
3,5-di-(branched alkyl)-4-hydroxythiolobenzoic acids, and
3,5-di-(branched alkyl)-4-hydroxydithiobenzoic acis are effective for the control of insects when applied in insecticidally effective amounts. The compounds of the present invention are particularly effective against mosquitoes. Although mosquito larvae treated with the compounds develop normally through the larval stage, metamorphosis is blocked in the pupal stage, and the insect dies or is sterilized.

DESCRIPTION OF THE INVENTION

The Benzoic Esters

The benzoates, thiolobenzoates, thionobenzoates, and dithiobenzoates are represented by the formula (I)

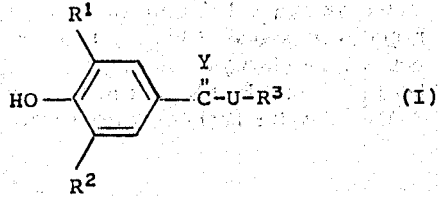

wherein Y is oxygen or sulfur; U is oxygen or sulfur; $R^1$ and $R^2$ are branched alkyl groups of 3 to 6 carbon atoms attached to the aromatic ring through a secondary or tertiary carbon atom; $R^3$ is: (1) alkyl of 1 to 6 carbon atoms, (2) cycloalkyl of 3 to 10 carbon atoms, (3) alkenyl of 3 to 6 carbon atoms, (4) alkynyl of 3 to 6 carbon atoms, (5) alkoxyalkyl of 2 to 6 carbon atoms, (6) alkylthioalkyl of 2 to 6 carbon atoms, (7) phenylalkyl of 7 to 12 carbon atoms, (8) phenylalkyl of 7 to 12 carbon atoms substituted on the phenyl ring with 1 to 2 substituents, preferably 1, selected from alkyl of 1 to 4 carbon atoms, alkoxy of 1 to 4 carbon atoms, fluorine, chlorine, bromine and alkylenedioxy of 1 to 4 carbon atoms, (9) alkyl of 1 to 4 carbon atoms (preferably methyl) substituted with a heterocyclic group having 1 to 2 rings, from 3 to 10 carbon atoms and 1 to 3 hetero atoms (e.g., O, S and N), or (10) a heterocyclic group having 1 to 2 rings, from 3 to 10 carbon atoms and 1 to 3 hetero atoms (e.g., O, S and N).

Representative branched alkyl groups which $R^1$ and $R^2$ may represent include s-propyl, s-butyl, t-butyl, t-amyl, s-hexyl, etc. $R^1$ and $R^2$ may be the same or different branched alkyl groups. Preferred $R^1$ and $R^2$ groups are attached to the aromatic ring through a secondary carbon atom (i.e., a carbon atom substituted with 2 alkyl groups) or a tertiary carbon atom (i.e., a carbon atom substituted with 3 alkyl groups). Tertiary-alkyl $R^1$ and $R^2$ groups are particularly preferred, especially t-butyl.

Suitable alkyl $R^3$ groups include methyl, ethyl, n-propyl, isopropyl, n-butyl, t-butyl, n-pentyl, isohexyl, etc. Preferred alkyl $R^3$ groups are tertiary alkyl groups of 4 to 6 carbon atoms, e.g., t-butyl, t-amyl, etc. Suitable cycloalkyl groups include cyclopropyl, cyclopropylmethyl, cyclobutyl, cyclopentyl, 1-cyclopentylethyl, cyclohexyl, cyclohexylmethyl, 2-cyclohexylethyl, cycloheptyl, cyclooctyl, etc. Preferred cycloalkyl groups are those having 5 to 8 carbon atoms. Suitable alkenyl $R^3$ groups include allyl, 2-butenyl, 3-hexenyl, etc. Preferred alkenyl groups are 2-alkenyl. Suitable alkynyl $R^3$ groups include propargyl, 2-butynyl, 3-pentynyl, etc. Preferred alkynyl groups are 2-alkynyl. Suitable alkoxy alkyl $R^3$ groups include methoxymethyl, ethoxyethyl, isopropoxypropyl, etc. Suitable alkylthioalkyl $R^3$ groups include methylthiomethyl, ethylthioethyl, n-propylthiopropyl, etc. Suitable substituted phenylalkyl $R^3$ groups include 4-methylbenzyl, 4-ethylbenzyl, 2-phenylethyl, 4-phenylbutyl, 3-t-butylbenzyl, 4-methoxybenzyl, 3,5-diethyloxybenzyl, 2-fluorobenzyl, 3-fluorophenylethyl, 2,4-difluorobenzyl, 4-chlorobenzyl, 2,4-dichlorobenzyl, 4-bromobenzyl, 3,4-methylenedioxybenzyl, 2,3-ethylenedioxybenzyl, 2-fluoro-4-methylbenzyl, 3-chloro-4-methoxybenzyl, etc. Substituted $R^3$ benzyl groups are preferably substituted in the meta or para position. Suitable heterocyclic-substituted alkyl $R^3$ groups include 2-thiophenemethyl, 3-thiophenemethyl, 2-(2-furanyl)ethyl, 3-furanylmethyl, 2-pyranylmethyl, 3-(3-pyranyl)propyl, 4-(2-pyranyl)butyl, 2-pyridylmethyl, 4-pyridylmethyl, 2-pyrrolylmethyl, 3-pyrrolylmethyl, 2-piperidylmethyl, 3-piperidylmethyl, 2-pyrrolinylmethyl, 2-imidazolymethyl, 5-imidazolidinylmethyl, 2-pyrazolylmethyl, 2-thiazolylmethyl, 5-thiazolidinylmethyl, etc. The preferred heterocyclic-substituted alkyl groups are heterocyclic-substituted methyl groups wherein the heterocyclic group is 5- to 6-membered monoheterocyclic groups, having 1 to 2 hetero atoms and 3 to 8 carbon atoms. Suitable heterocyclic $R^3$ groups include 3-isoxazolyl, 5-isoxazolinyl, 2-thiazolyl, 2-thiazolinyl, 3-pyrazolyl, 2-imidazolyl, 2-pyrrolyl, 2-furanyl, 2-thiophene 2-(7-methylbenzoxazolyl), 2-benzothiazolyl, 2-benzimidazolyl, 2-indolyl, 1-isoindolyl, 7-(2,2-dimethyl-2,3-dihydrobenzofuranyl), etc. The preferred heterocyclic groups are 5- to 6-membered monoheterocyclic groups having 1 to 2 hetero atoms and 3 to 8 carbon atoms.

Illustrative thiolobenzoates (Y is oxygen and U is sulfur) of formula I include:

methyl 3,5-di-s-propyl-4-hydroxythiolobenzoate,
ethyl 3-s-propyl-5-t-butyl-4-hydroxythiolobenzoate,
t-butyl-3,5-di-t-butyl-4-hydroxythiolobenzoate,
t-amyl 3,5-di-t-butyl-4-hydroxythiolobenzoate,
allyl 3,5-di-t-butyl-4-hydroxythiolobenzoate,
2-pentenyl 3,5-di-t-amyl-4-hydroxythiolobenzoate,
propargyl 3,5-di-s-butyl-4-hydroxythiolobenzoate,
2-hexynyl 3,5-di-t-butyl-4-hydroxythiolobenzoate,
methoxymethyl 3,5-di-t-amyl-4-hydroxythiolobenzoate,
isopropylthiomethyl 3,5-di-t-butyl-4-hydroxythiolobenzoate,
benzyl 3,5-di-t-butyl-4-hydroxythiolobenzoate,
benzyl 3-t-amyl-5-t-butyl-4-hydroxythiolobenzoate,
benzyl 3,5-di-t-amyl-4-hydroxythiolobenzoate,
3-phenylpropyl 3,5-di-t-butyl-4-hydroxythiolobenzoate,
2-tolylethyl 3,5-di-t-butyl-4-hydroxythiolobenzoate,
4-fluorobenzyl 3,5-di-t-butyl-4-hydroxythiolobenzoate,
3,5-difluorobenzyl 3,5-di-t-butyl-4-hydroxythiolobenzoate,
4-chlorobenzyl 3,5-di-t-butyl-4-hydroxythiolobenzoate,
3-fluoro-4-chlorobenzyl 3,5-di-t-amyl-4-hydroxythiolobenzoate,
3-methyl-4-chlorobenzyl 3,5-di-t-butyl-4-hydroxythiolobenzoate,
3,4-methylenedioxybenzyl 3,5-di-s-propyl-4-hydroxythiolobenzoate,
3,4-methylenedioxybenzyl 3,5-di-t-butyl-4-hydroxythiolobenzoate
2-(3-methylthiophene)methyl 3,5-di-t-butyl-4-hydroxythiolobenzoate,
2-(3-methylpyridyl)methyl 3,5-di-t-butyl-4-hydroxythiolobenzoate,
2-(3-methylfuran-2-yl)ethyl 3,5-di-t-butyl-4-hydroxythiolobenzoate,
2-piperidylmethyl 3,5-di-t-butyl-4-hydroxythiolobenzoate,
2-pyranylmethyl 3,5-di-t-butyl-4-hydroxythiolobenzoate,
2-imidazolylmethyl 3,5-di-t-butyl-4-hydroxythiolobenzoate,
2-imidazolidinylmethyl 3,5-di-t-butyl-4-hydroxythiolobenzoate,
2-pyrrolylmethyl 3,5-di-t-butyl-4-hydroxythiolobenzoate,
2-pyrrolinylmethyl 3,5-di-t-butyl-4-hydroxythiolobenzoate,
2-pyrazolylmethyl 3,5-di-t-butyl-4-hydroxythiolobenzoate,
2-benzimidazolylmethyl 3,5-di-t-butyl-4-hydroxythiolobenzoate,
2-thiazolyl 3,5-di-t-butyl-4-hydroxythiolobenzoate,
2-thiazolidinyl 3,5-di-t-butyl-4-hydroxythiolobenzoate.

Illustrative dithiobenzoates (Y and U are sulfur) of formula I include:

propyl 3,5-di-t-butyl-4-hydroxydithiobenzoate,
t-butyl 3,5-di-t-butyl-4-hydroxydithiobenzoate,
cyclohexylmethyl 3,5-di-t-butyl-4-hydroxydithiobenzoate,
allyl 3,5-di-t-butyl-4-hydroxydithiobenzoate,
propargyl 3,5-di-t-amyl-4-hydroxydithiobenzoate,
ethoxymethyl 3,5-di-s-amyl-4-hydroxydithiobenzoate,
ethylthiomethyl 3,5-di-t-butyl-4-hydroxydithiobenzoate,
α-methylbenzyl 3,5-di-t-butyl-4-hydroxydithiobenzoate,
2-phenylethyl 3,5-di-t-amyl-4-hydroxydithiobenzoate,
4-t-butylbenzyl 3,5-di-t-butyl-4-hydroxydithiobenzoate,
2,4-difluorobenzyl 3,5-di-t-butyl-4-hydroxydithiobenzoate,
4-chlorobenzyl 3,5-di-t-butyl-4-hydroxydithiobenzoate,
3-chloro-4-bromobenzyl 3,5-di-t-butyl-4-hydroxydithiobenzoate,
3,4-methylenedioxybenzyl 3,5-di-t-butyl-4-hydroxydithiobenzoate,
2-thiophenemethyl 3,5-di-t-butyl-4-hydroxydithiobenzoate,
2-pyridyl 3,5-di-t-butyl-4-hydroxydithiobenzoate,
2-furanylmethyl 3,5-di-t-butyl-4-hydroxydithiobenzoate,
2-piperidylmethyl 3,5-di-t-butyl-4-hydroxydithiobenzoate,
2-pyranylmethyl 3,5-di-t-butyl-4-hydroxydithiobenzoate,
2-imidazolylmethyl 3,5-di-t-butyl-4-hydroxydithiobenzoate,
2-imidazolidinylmethyl 3,5-di-t-butyl-4-hydroxydithiobenzoate,
2-pyrrolylmethyl 3,5-di-t-butyl-4-hydroxydithiobenzoate,
2-pyrrolinylmethyl 3,5-di-t-butyl-4-hydroxydithiobenzoate,
2-pyrazolyl 3,5-di-t-butyl-4-hydroxydithiobenzoate,
2-thiazolylmethyl 3,5-di-t-butyl-4-hydroxydithiobenzoate,
2-thiazolidinylmethyl 3,5-di-t-butyl-4-hydroxydithiobenzoate.

Illustrative benzoates of formula I (Y and U are oxygen) include:

methyl 3,5-di-t-butyl-4-hydroxybenzoate,
t-butyl-3,5-di-s-propyl-4-hydroxybenzoate,
ethyl 3-s-propyl-5-t-butyl-4-hydroxybenzoate,
t-butyl 3,5-di-t-butyl-4-hydroxybenzoate,
t-amyl 3,5-di-t-butyl-4-hydroxybenzoate,
allyl 3,5-di-t-butyl-4-hydroxybenzoate,
2-pentenyl 3,5-di-t-amyl-4-hydroxybenzoate,
propargyl 3,5-di-s-butyl-4-hydroxybenzoate,
2-hexynyl 3,5-di-t-butyl-4-hydroxybenzoate,
methoxymethyl 3,5-di-t-amyl-4-hydroxybenzoate,
isopropylthiomethyl 3,5-di-t-butyl-4-hydroxybenzoate,
benzyl 3,5-di-t-butyl-4-hydroxybenzoate,
benzyl 3-t-amyl-5-t-butyl-4-hydroxybenzoate,
benzyl 3,5-di-t-amyl-4-hydroxybenzoate, 4-methylbenzyl 3,5-di-t-butyl-4-hydroxybenzoate,
3,5-dimethylbenzyl 3,5-di-t-butyl-4-hydroxybenzoate,
4-fluorobenzyl 3,5-t-butyl-4-hydroxybenzoate,
3,5-difluorobenzyl 3,5-di-t-butyl-4-hydroxybenzoate,
4-chlorobenzyl 3,5-di-t-butyl-4-hydroxybenzoate,
3-fluoro-4-chlorobenzyl 3,5-di-t-amyl-4-hydroxybenzoate,
3-methyl-4-chlorobenzyl 3,5-di-s-butyl-4-hydroxybenzoate,
3,4-methylenedioxybenzyl 3,5-di-s-propyl-4-hydroxybenzoate,
3,4-methylenedioxybenzyl 3,5-di-t-butyl-4-hydroxybenzoate,
2-thiophenemethyl 3,5-di-t-butyl-4-hydroxybenzoate,
2-pyridyl 3,5-di-t-butyl-4-hydroxybenzoate,
2-furanylmethyl 3,5-di-t-butyl-4-hydroxybenzoate,
2-piperidylmethyl 3,5-di-t-butyl-4-hydroxybenzoate,
2-pyranylmethyl 3,5-di-t-butyl-4-hydroxybenzoate,
2-imidazolylmethyl 3,5-di-t-butyl-4-hydroxybenzoate,
2-imidazolidinylmethyl 3,5-di-t-butyl-4-hydroxybenzoate,
2-pyrrolylmethyl 3,5-di-t-butyl-4-hydroxybenzoate,
2-pyrrolinylmethyl 3,5-di-t-butyl-4-hydroxybenzoate,
2-pyrazolylmethyl 3,5-di-t-butyl-4-hydroxybenzoate,
2-thiozolylmethyl 3,5-di-t-butyl-4-hydroxybenzoate,
2-thiazolidinylmethyl 3,5-di-t-butyl-4-hydroxybenzoate.

Additional compounds of formula I having heterocyclic $R^3$ groups include:

2-benzothiazolyl 3,5-di-t-butyl-4-hydroxythiolobenzoate,
2-benzimidazolyl 3,5-di-t-butyl-4-hydroxythiolobenzoate,
2-thiophene 3,5-di-t-butyl-4-hydroxydithiobenzoate,
7-(2,2-dimethyl-2,3-dihydrobenzofuranyl) 3,5-di-t-butyl-4-hydroxybenzoate,
7-(2,2-dimethyl-2,3-dihydrobenzofuranyl) 3,5-di-t-butyl-4-hydroxythiolobenzoate.

The thiolobenzoates of formula I may exist in their tautomeric form, i.e., as thionobenzoates (wherein Y is sulfur and U is oxygen). Such tautomers of the thiolobenzoates are suitably employed in the method of the invention.

The dithiobenzoates and thiolobenzoates of formula I are prepared by reaction of a dithiobenzoate or thiolobenzoate salt and an organic halide corresponding to the $R^3$ group as depicted in the following equation 1:

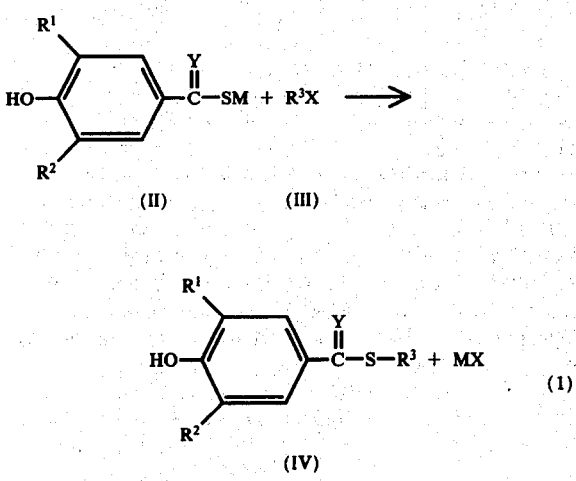

wherein $R^1$, $R^2$, $R^3$ and Y have the same significance as defined above, M is a metal cation, preferably an alkali metal cation, e.g., sodium or potassium, and X is a halogen, preferably chlorine or bromine.

The reaction depicted in equation 1 is conducted by conventional procedures. The molar ratio of dithiobenzoate or thiolobenzoate salt to $R^3X$ is substantially equimolar. The reaction is conducted in inert solvents, preferably aprotic solvents having high dielectric constants, such as dimethoxyethane, dimethylsulfoxide, etc. Reaction temperatures suitably vary from 0° to 150° C. The product is generally obtained by evaporating or distilling off the solvent after the reaction mixture has been washed with water to remove by-product salts. The product is then purified by recrystallizaton, chromatography, etc.

Dithiobenzoate and thiolobenzoate salts of formula II are suitably prepared from the corresponding dithiobenzoic or thiolobenzoic acid and an alkali metal hydroxide solution. Alternatively, the dithiobenzoate salts are prepared directly from 3,5-di-(branched alkyl)phenols and carbon disulfide by known procedures, as disclosed, for example, by Gomper, Schmidt and Kutter, *Liebigs Annalin*, Bd 684, 37 (1965).

The thiolobenzoates and benzoates of formula I also are prepared by the reaction of a benzoyl halide and a mercaptan or an alcohol corresponding to the $R^3$ group in the presence of an acid acceptor, as depicted in the following equation 2:

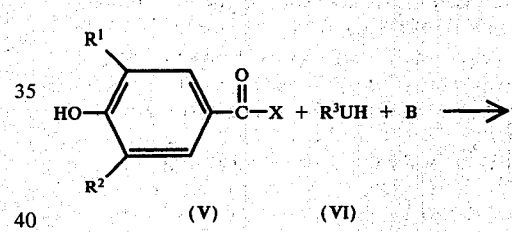

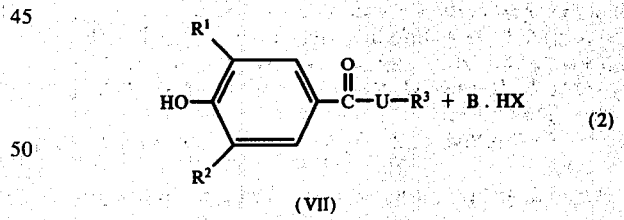

wherein $R^1$, $R^2$, $R^3$, X and U have the same significance as defined above, and B is an acid acceptor.

The reaction depicted in equation 2 is conducted by conventional procedures. Molar ratios of the reactants are substantially equimolar. Suitable acid acceptors include organic bases such as pyridine and trialkylamines, e.g., triethylamine. Inert solvents are generally employed. Reaction temperatures vary from 0° to 150° C. The product is isolated by conventional methods such as extraction, distillation, crystallizaton, etc.

Certain dithiobenzoates and thiolobenzoates of formula I are also prepared by the addition of a dithiobenzoic or thiolobenzoic acid to an olefin, as depicted in the following equation 3:

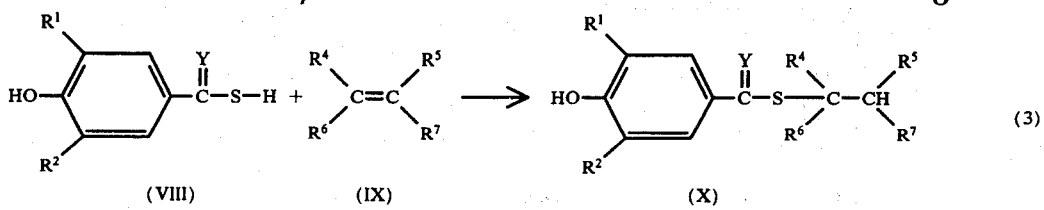

(3)

wherein $R^1$, $R^2$ and Y have the same significance as previously defined; $R^4$ and $R^5$ are hydrogen or alkyl of 1 to 4 carbon atoms; $R^6$ and $R^7$ individually are hydrogen, alkyl of 1 to 4 carbon atoms, phenyl, phenyl substituted with 1 to 2 substituents selected from alkyl, alkoxy, fluorine, chlorine or alkylenedioxy, or heterocyclic of 3 to 10 carbon atoms and 1 to 3 hetero atoms (O, S or N), with the proviso that only one $R^6$ or $R^7$ group is alkyl, phenyl, substituted phenyl or heterocyclic.

It is appreciated that the

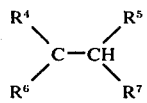

moiety corresponds to certain $R^3$ groups. For example, the addition reaction depicted in equation 3 can be employed to prepare compounds of formula I wherein $R^3$ is alkyl, e.g., the addition of 3,5-di-t-butyl-4-hydroxythiolobenzoic acid to isobutylene to give t-butyl 3,5-di-t-butyl-4-hydroxythiolobenzoate; wherein $R^3$ is phenylalkyl, e.g., the addition of 3,5-di-t-butyl-4-hydroxythiolobenzoic acid to styrene to give 2-phenylethyl 3,5-di-t-butyl-4-hydroxythiolobenzoate; and wherein $R^3$ is heterocyclic-substituted alkyl, e.g., the addition of 3,5-di-t-butyl-4-hydroxydithiobenzoic acid to vinylpyridine to give pyridylethyl 3,5-di-t-butyl-4-hydroxydithiobenzoate.

Addition reaction 3 is conducted by contacting the dithiobenzoic or thiolobenzoic acid and the olefin compound (IX) in molar ratios of about 1:3 to 3:1 in an inert solvent at a temperature of about 50° to 150° C. Suitable inert solvents include aromatic hydrocarbons such as benzene, toluene and xylene. The addition product is isolated and purified by methods such as extraction, distillation, crystallization, chromatography, etc.

Insect Control

The compounds of the present invention are useful as insecticides, particularly as morphogenetic hormonal mimetic insecticides; that is, they inhibit the normal growth pattern (maturation) of certain insects, thereby limiting reproduction of those insects.

In addition to mosquitoes, the compounds of the invention have morphogenetic hormonal mimetic activity on insects such as houseflies (*Musca domestica* L.), yellow mealworm (*Tenelrio molitor*), cabbage looper (*Trichoplusia ni*) and kissing bug (*Rhodnius prolixus*).

The compounds are very potent and are used at extremely low concentrations. For example, compositions containing 100 ppm to 0.01 ppm, preferably from 5 ppm to 0.1 ppm, are effective for the control of insects. However, the effective concentration depends in part on the mode of application and the particular insect.

The compounds may be applied in either liquid or solid formulations to the pre-adult insects or their environment. For example, they may be sprayed or otherwise applied directly to plants or aqueous bodies so as to effect control of insects coming into contact therewith.

Formulations of the compounds of this invention will comprise a toxic amount of one or more of the compounds and a biologically inert carrier. Usually they will also contain a wetting agent. Solid carriers such as clay, talc, sawdust, alfalfa meal, and the like may be used in such formulations. Liquid diluents which may be used with these compounds include water with appropriate emulsifying agents and aromatic solvents. In addition, these formulations may contain other compatible pesticides, fillers, stabilizers, attractants. and the like.

The concentration of the active ingredient to be used with inert carriers, either solid or liquid carriers, will be dependent upon many factors, such as the particular compound which is used, the carrier in or upon which it is incorporated, the method and conditions of application, the insect species to be controlled, etc., the proper consideration of these factors being within the skill of those versed in the art. In general, the toxic ingredients of this invention will be effective in concentrations from about 0.0001% by weight to as high as 50% by weight, or higher.

The compounds of the invention are particularly useful in combination with mosquito larvicidal petroleum oil dispersions. Petroleum oils suitable as mosquito larvicidal dispersions are known. Such hydrocarbon oils include mineral oils such as naphthenic base and paraffinic base lubricating oils, etc., as well as synthetic oils. Such hydrocarbon oils are non-phytotoxic and generally contain not more than a few percent aromatics. Particularly suitable hydrocarbon oils have boiling points above 350° to 400° F. and viscosities from about 33 to 200 SSU at 100° F.

The amount of the compound of the invention employed in petroleum oil generally ranges from 0.1% to 10% by weight, based on weight of oil. The hydrocarbon oil dispersions containing the compounds of the invention are contacted with or applied to the surface of the aqueous bodies wherein mosquito control is desired by conventional methods.

The terms "insecticide" and "insect" as used herein refer to their broad and commonly understood usage rather than to those creatures which in the strict biological sense are classified as insects. Thus, the term "insect" is used not only to include small invertebrate animals belonging to the class Insecta, but also to other related classes of arthropods whose members are segmented invertebrates having more or fewer then 6 legs, such as spiders, mites, ticks, centipedes, worms and the like.

EXAMPLES

Example 1 — Preparation of benzyl 3,5-di-t-butyl-4-hydroxythiobenzoate

A flask was charged with 0.3 mol of 2,6-di-t-butylphenol and 150 ml of dimethylsulfoxide. To the flask, maintained at 10° C., was added dropwise an aqeuous solution of 0.6 mol potassium hydroxide, followed by 0.3 mol carbon disulfide. The resulting reaction mixture was stirred at 10° C. for 1 hour and then allowed to warm to about 25° C. Concentrated hydrochloric acid (0.3 mol) was then addead slowly to the reaction mixture, maintained at 0° C. Benzylbromide (0.3 mol) was then added and the reaction mixture heated at 50° C. for 1 hour. The reaction mixture was coold, diluted with 600 ml ice water, and extracted with ether. The ether extracts were washed with water, dried over magnesium sulfate and evaporated to give the crude product. After crystallization from hexane, the product melted at 110°–112° C. Elemental analysis of the product is tabulated in Table I. The product is believed to be novel.

Example 2 — Preparation of allyl 3,5-di-t-butyl-4-hydroxydithiobenzoate

A 0.1 mol sample of 2,6-di-t-butylphenol was added dropwise to a solution of 0.2 mol sodium hydride (57% in mineral oil) in 150 ml dimethoxyethane under an atmosphere of nitrogen at about 25° C. After the addition was completed, the reaction mixture was stirred for one hour at 25° C. A 0.1 mol sample of carbon disulfide was then added and the resulting reaction mixture stirred at about 25° C. for 10 minutes. Concentrated hydrochloric acid (0.1 mol) was added slowly, followed by 0.1 mol allyl bromide in 50 ml dimethoxyethane. The reaction mixture was then heated at reflux overnight (about 16 hours). The reaction mixture was poured into ice water and the crystalline product recovered by filtration. Recrystallization from ether/hexane gave the product, which melted at 93°–95° C. Elemental analysis of the product is tabulated in Table I.

Example 3 — Preparation of t-butyl 3,5-di-t-butyl-4-hydroxythiolobenzoate t-Butyl mercaptan (0.05 mol) was added slowly to a flask containing 0.05 mol 2,6-di-t-butyl-4-hydroxybenzoyl chloroide (m.p. 96°–98° C.) and 0.05 mol pyridine in 250 ml. dimethoxyethane. After the addition was completed, the reaction mixture was refluxed. The reaction mixture was then diluted with ice water, extracted with methylene dichloride and evaporated. The residue was chromatographed on silica gel (hexane/ether eluants) to give the product, m.p. 117°–120° C. Elemental analysis of the product is tabulated in Table I.

Example 4 — Preparation of benzyl 3,5-di-t-butyl-4-hydroxybenzoate

To a flask containing 0.1 mol sodium 2,6-di-t-butyl-4-hydroxybenzoate in 200 ml dimethoxyethane was added dropwise 0.1 mol of benzyl chloride. The reaction mixture was refluxed. The reaction mixture was then diluted with ether, washed with water, dried over magnesium sulfate and evaporated to give the crude product. Recrystallization from hexane gave the product, which melted at 80°–83° C. Elemental analysis of the product is tabulated in Table I.

Example 5 — Preparation of 2-Thiophenemethyl 3,5-di-t-butyl-4-hydroxybenzoate A solution of 0.1 mol 2,6-di-t-butyl-4-hydroxybenzoyl chloride, 0.1 mol 2-hydroxymethylthiophene, and 0.1 mol pyridine in 200 ml dimethoxyethane was refluxed for 1 hour. The reaction mixture was filtered to remove precipitated pyridine hydrochloride, poured onto ice, extracted with ether, dried over magnesium sulfate and evaporated under reduced pressure to give a yellow, solid residue. The residue was recrystallized from hexane to give the product, m.p. 74°–78° C. Elemental analysis of the product is tabulated in Table I.

Example 6 — Preparation of 2-thiophenemethyl 3,5-di-t-butyl-4-hydroxydithiobenzoate 0.1 mol of 2,6-di-t-butylphenol was added dropwise to a solution of 0.2 mol sodium hydride (57% in mineral oil) in 150 ml of dimethoxyethane, under an atmosphere of nitrogen at about 25° C. After the addition was completed, the reaction mixture was stirred for 1 hour at 25° C. A 0.1 mol sample of carbon disulfide was then added and the resulting reaction mixture stirred at about 25° C. for 10 minutes. Concentrated hydrochloric acid (0.1 mol) was added slowly, followed by 0.1 mol 2-(chloromethyl)lthiophene in 50 ml of dimethoxyethane. The reaction mixture was then heated at reflux overnight (about 16 hours). The reaction mixture was poured into ice water and the crystalline product recovered by filtration. Recrystallization from ether/hexane gave the product, which melted at 104°–107° C. Elemental analysis of the product is tabulated in Table I.

Example 7 — Preparation of 3,4-dichlorobenzyl 3,5-di-t-butyl-4-hydroxythiolobenzoate A solution of 6.66 g (0.025 mol) 3,5-di-t-butyl-4-hydroxythiolobenzoic acid in 125 ml dimethylsulfoxide was added to 1.05 g (0.025 mol) sodium hydride. The mixture was heated slightly to obtain a homogeneous solution of the sodium thiolobenzoate. 4.89 g (0.025 mol) of 3,4-dichlorobenzyl chloride was then added dropwise to the solution of sodium thiolobenzoate. The reaction mixture was then heated at 75° C. for about 1 hour, cooled, poured in an ice/water mixture, and extracted with methylene dichloride. The methylene dichloride extracts were dried over magnesium sulfate and evaporated under reduced pressure. The resulting oil crystallized on storage at 0° C. to give the crude product. The crude product was purified by chromatography on silica gel with hexane eluant. The purified product melted at 103°–105° C. Elemental analysis of the product is tabulated in Table I.

Example 8 — Preparation of 2-(Δ²-thiazolinyl) 3,5-di-t-butyl-4-hydroxythiolobenzoate A solution of 13.44 g (0.05 mol 3,5-di-t-butyl-4-hydroxybenzoyl chloride, 5.96 g (0.05 mol) 2-mercapto-Δ²-thiazoline and 4.0 g (0.05 mol) pyridine in 100 ml dimethoxyethane was refluxed for 1 hour. The reaction mixture was diluted with ice water and extracted with diethyl ether. The ether extracts were dried over magnesium sulfate and evaporated under reduced pressure. The residue was crystallized from hexane/diethyl ether to give the product, m.p. 158°–160° C. Elemental analysis of the product is tabulated in Table I.

Example 9 — Preparation of α,α-dimethylbenzyl 3,5-di-t-butyl-4-hydroxydithiobenzoate A solution of 16.25 g (0.0575 mol) 3,5-di-t-butyl-4-hydroxydithiobenzoic acid and 13.6 g (0.115 mol α-methylstyrene in 50 ml toluene was heated at reflux for 2 hours. The reaction mixture was evaporated under reduced pressure to give an oil. The oil was chromatographed on silica gel (hexane eluant) to give the product, m.p. 100°–104° C. Elemental analysis of the product is tabulated in Table I.

Example 10 — Preparation of α-methylbenzyl 3,5-di-t-butyl-4-hydroxydithiobenzoate A solution of 14.1 g (0.05 mol) 3,5-di-t-butyl-4-hydroxydithiobenzoic acid and 10.4 g (0.1 mol) styrene in 100 ml toluene was heated at reflux for about 1 hour. The reaction mixture was filtered through silica gel and evaporated under reduced pressure to give the product, m.p. 70°–72° C. Elemental analysis of the product is tabulated in Table I.

Example 11 — Preparation of t-butyl 3,5-di-t-butyl-4-hydroxydithiobenzoate

A solution of 14.1 g (0.05 mol) 3,5-di-t-butyl-4-hydroxydithiobenzoic acid and 5.6 g (0.1 mol) isobutylene in 20 ml toluene was placed in a glass bomb tube. The tube was sealed and heated at 110° C. for 2 hours. The tube was cooled and opened. The contents were removed and evaporated under reduced pressure to give the product as an orange solid, m.p. 128°–130° C. Elemental analysis of the product is tabulated in Table I.

Example 12 — Preparation of 2-phenylpropyl 3,5-di-t-butyl-4-hydroxythiolobenzoate A solution of 6.66 g (0.025 mol) 3,5-di-t-butyl-4-hydroxythiolobenzoic acid and 5.9 g (0.05 mol) α-methylstyrene in about 50 ml xylene was heated at reflux for 6 hours. The reaction mixture evaporated under reduced pressure. The resulting oil was placed on a silica-gel column. Elution with hexane followed by methylene dichloride gave the product (via anti-Markovnikov addition), m.p. 108°–112° C. The nuclear magnetic resonance spectrum of the product showed the methylene protons of the

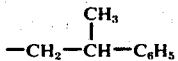

moiety as a doublet at 3.3δ and the methyl protons of the

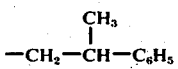

moiety as a doublet at 1.5δ. Elemental analysis of the product is tabulated in Table I.

Example 13 — Preparation of 2-phenylethyl 3,5-di-t-butyl-4-hydroxythiolobenzoate A solution of 6.66 g (0.025 mol) 3,5-di-t-butyl-4-hydroxythiolobenzoic acid and 5.2 g (0.05 mol) styrene in about 50 ml of toluene was sealed in a glass bomb tube and heated at 120° C. over night. The reaction mixture was eluted through a silica-gel column to give the product (via anti-Markovnikov addition), as a white solid, m.p. 89°–91° C. The elemental analysis of the product is tabulated in Table I.

Example 14 — Preparation of 2-(4-pyridyl)ethyl 3,5-di-t-butyl-4-hydroxydithiobenzoate A solution of 6.6 g (0.062 mol) 4-vinylpyridine and 14.1 g (0.05 mol) 3,5-di-t-butyl-4-hydroxydithiobenzoic acid in 50 ml toluene was refluxed for 6 hours. On cooling, the product (via anti-Markovnikov addition) crystallized from the reaction mixture. After recrystallization from chloroform, the product melted at 191°–193° C. Elemental analysis of the product is tabulated in Table I.

Example 15 — Preparation of 1-[1-(2-pyrrolidone)]ethyl 3,5-di-t-butyl-4-hydroxydithiobenzoate

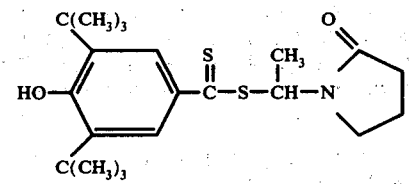

A solution of 6.9 g (0.062 mol) of N-vinyl-2-pyrrolidone and 14.1 g (0.05 mol) 3,5-di-t-butyl-4-hydroxydithiobenzoic acid in 50 ml toluene was refluxed for 6 hours. Most of the toluene was then removed from the reaction mixture by evaporation under reduced pressure. The product, m.p. 149°–151° C., crystallized from the resulting residue. The elemental analysis of the product is tabulated in Table I.

Example 16 — Preparation of 2-pyridyl 3,5-di-t-butyl-4-hydroxythiolobenzoate A solution of 13.44 g (0.05 mol 3,5-di-t-butyl-4-hydroxybenzoyl chloride, 5.56 g (0.05 mol) 2-mercaptopyridine, and 4.0 g (0.05 mol) pyridine in 100 ml dimethoxyethane was heated at reflux until pyridine hydrochloride formation ceased. The reaction mixture was filtered and then extracted with methylene dichloride. The methylene dichloride extracts were dried over magnesium sulfate, decolorized with activated carbon black and evaporated to give the product as white crystals, m.p. 138°–140° C. The elemental analysis of the product is tabulated in Table I.

Example 17 — Preparation of 3,5-di-t-butyl-4-hydroxythiolobenzoic acid

A solution of 41.26 g (0.2 mol) 2,6-di-t-butylphenol in 250 ml dimethoxyethane was added to a slurry of 16.84 g (0.4 mol) sodium hydride in 50 ml dimethoxyethane. The reaction mixture was stirred for 1 hour at about 25° C. A solution (cooled to −50° C.) of 25 ml carbon oxysulfide and 25 ml dimethoxyethane was then added to the reaction mixture. The reaction mixture was stirred and allowed to warm to about 25° C. Stirring was continued for 3 hours at 25° C. 0.04 mol of dilute aqueous acid was added to the reaction mixture with vigorous stirring while the mixture was cooled in ice water. The reaction mixture was then poured into an ice/water mixture. The resulting precipitate was filtered, dissolved in methylene dichloride washed with water, dried over magnesium sulfate and evaporated under reduced pressure to give the product as a pink solid, m.p. 137°–139° C. Elemental analysis for $C_{15}H_2SO_2$ showed: %S, calc. 12.0, found 12.2.

Other compounds were prepared from appropriate starting materials using the procedures described in Examples 1–16. These compounds are also tabulated in Table I. The method of preparation, i.e., according to reaction 1, 2 or 3, as heretofore described, is indicated in the first column of the Table.

concentration and the mortality counts are tabulated in Table II.

TABLE I

| Rxn No. | COMPOUND | MELTING POINT, °C. | Sulfur, Wt.% Calc. | Sulfur, Wt.% Found | Halogen, Wt.% Calc. | Halogen, Wt.% Found |
|---|---|---|---|---|---|---|
| 1 | 3,4-methylenedioxybenzyl 3,5-di-t-butyl-4-hydroxydithiobenzoate | 118 | 15.4 | 14.7 | — | — |
| 1 | benzyl 3,5-di-t-butyl-4-hydroxythiolobenzoate | 122–124 | 9.0 | 8.9 | — | — |
| 2 | benzyl 3,5-di-t-butyl-4-hydroxydithiobenzoate | 110–112 | 17.3 | 16.4 | — | — |
| 1 | benzyl 3,5-di-t-butyl-4-hydroxybenzoate | 80–83 | — | — | — | — |
| 2 | 2-thiophenemethyl 3,5-di-t-butyl-4-hydroxybenzoate | 74–78 | 9.3 | 8.8 | — | — |
| 1 | 2-thiophenemethyl 3,5-di-t-butyl-4-hydroxydithiobenzoate | 104–107 | 25.4 | 23.2 | — | — |
| 1 | 3,4-dichlorophenyl 3,5-di-t-butyl-4-hydroxydithiobenzoate | 103–105 | 7.54 | 7.0 | 16.7(Cl) | 16.0 |
| 2 | 2-($\Delta^2$-thiazolinyl) 3,5-di-t-butyl-4-hydroxythiolobenzoate | 158–160 | 18.25 | 18.01 | — | — |
| 3 | α,α-dimethylbenzyl 3,5-di-t-butyl-4-hydroxydithiobenzoate | 100–104 | 16.0 | 16.1 | — | — |
| 3 | α-methylbenzyl 3,5-di-t-butyl-4-hydroxythiobenzoate | 70–72 | 16.6 | 15.7 | — | — |
| 3 | t-butyl 3,5-di-t-butyl-4-hydroxydithiobenzoate | 128–130 | 18.9 | 18.8 | — | — |
| 3 | 2-phenylpropyl 3,5-di-t-butyl-4-hydroxythiolobenzoate | 108–112 | 8.32 | 8.5 | — | — |
| 3 | 2-phenylethyl 3,5-di-t-butyl-4-hydroxythiolobenzoate | 89–91 | 8.66 | 8.6 | — | — |
| 3 | 2-(4-pyridyl)ethyl 3,5-di-t-butyl-4-hydroxydithiobenzoate | 191–193 | 16.5 | 17.5 | — | — |
| 3 | 1-[1-(2-pyrrolidone)]ethyl 3,5-di-t-butyl-4-hydroxydithiobenzoate | 149–151 | 16.3 | 16.1 | — | — |
| 2 | 2-pyridyl 3,5-di-t-butyl-4-hydroxythiolobenzoate | 138–140 | 9.35 | 9.52 | — | — |
| 2 | 2,6-dichlorobenzyl 3,5-di-t-butyl-4-hydroxythiolobenzoate | 117–119 | 7.53 | 7.6 | 16.7(Cl) | 16.6 |
| 1 | p-chlorobenzyl 3,5-di-t-butyl-4-hydroxydithiobenzoate | 107–109 | 16.2 | 15.7 | 8.9(Cl) | 8.7 |
| 2 | p-chlorobenzyl 3,5-di-t-butyl-4-hydroxythiolobenzoate | 117–120 | 8.2 | 8.4 | 9.1(Cl) | 9.0 |
| 1 | p-methoxybenzyl 3,5-di-t-butyl-4-hydroxydithiobenzoate | 122–125 | 15.9 | 15.6 | — | — |
| 1 | m-fluorobenzyl 3,5-di-t-butyl-4-hydroxydithiobenzoate | 90–93 | 16.4 | 16.3 | 4.9(F) | 5.0 |
| 1 | o-fluorobenzyl 3,5-di-t-butyl-4-hydroxydithiobenzoate | 124–127 | 16.4 | 16.2 | 4.9(F) | 5.0 |
| 1 | p-fluorobenzyl 3,5-di-t-butyl-4-hydroxydithiobenzoate | 94–96 | 16.4 | 16.3 | 4.9(F) | 5.0 |
| 1 | p-ethylbenzyl 3,5-di-t-butyl-4-hydroxydithiobenzoate | liquid | 16.0 | 15.7 | — | — |
| 1 | methyl 3,5-di-t-butyl-4-hydroxydithiobenzoate | 110–112 | 21.6 | 21.7 | — | — |
| 2 | methyl 3,5-di-t-butyl-4-hydroxythiolobenzoate | 138–140 | 11.4 | 11.6 | — | — |
| 2 | t-butyl 3,5-di-t-butyl-4-hydroxythiolobenzoate | 151–153 | 9.9 | 9.4 | — | — |
| 1 | allyl 3,5-di-t-butyl-4-hydroxydithiobenzoate | 93–95 | 19.9 | 19.5 | — | — |
| 1 | propargyl 3,5-di-t-butyl-4-hydroxydithiobenzoate | 110–113 | 20.0 | 19.5 | — | — |
| 1 | methoxymethyl 3,5-di-t-butyl-4-hydroxydithiobenzoate | 62–64 | 19.6 | 18.7 | — | — |
| 1 | methylthiomethyl 3,5-di-t-butyl-4-hydroxydithiobenzoate | 65–67 | 28.1 | 27.7 | — | — |
| 2 | 2-thiophenemethyl 3,5-di-t-butyl-4-hydroxythiolobenzoate | 121–123 | 17.7 | 16.3 | — | — |
| 2 | 2-thiazolinyl 3,5-di-t-butyl-4-hydroxythiolobenzoate | 158–160 | 18.25 | 18.01 | — | — |
| 1 | 3-pyridylmethyl 3,5-di-t-butyl-4-hydroxydithiobenzoate | 137–139 | 17.17 | 16.35 | — | — |
| 1 | 2-pyridylmethyl 3,5-di-t-butyl-4-hydroxydithiobenzoate | 79–82 | 17.17 | 16.58 | — | — |
| 2 | 2-pyridyl-N-oxide 3,5-di-t-butyl-4-hydroxythiolobenzoate | 155–158 | 8.94 | 8.53 | — | — |
| 2 | 3-pyridylmethyl 3,5-di-t-butyl-4-hydroxythiolobenzoate | 130–131 | 8.96 | 8.94 | — | — |
| 2 | 2-pyridylmethyl 3,5-di-t-butyl-4-hydroxythiolobenzoate | oil | 8.96 | 8.76 | — | — |
| 2 | 2-(1-methylimidazolyl) 3,5-di-t-butyl-4-hydroxythiolobenzoate | 126–129 | 9.25 | 9.25 | — | — |
| 2 | 2-benzoxazolyl 3,5-di-t-butyl-4-hydroxythiolobenzoate | 124–127 | 8.36 | 7.76 | — | — |
| 2 | 2-furanyl 3,5-di-t-butyl-4-hydroxythiolobenzoate | 93–96 | 9.25 | 9.50 | — | — |

Example 18 — Mosquito Control

The compounds of the present invention were tested as morphogenetic hormonal mimetic insecticides against Yellow Fever Mosquito larvae (*Aedes aegypti*) by the following procedures: Late-fourth-stage larvae of the mosquito are placed in a cup containing 30 ml of deionized water containing a known amount of the test compound dissolved therein. About 20 larvae are used per test. The larvae are fed and allowed to pupate. The live pupae are kept until the adult mosquito emerges. A count is made at each step for mortality, i.e., larval, pupal and adult mortality. The compound tested, the concentration and the mortality counts are tabulated in Table II.

Example 19 — Residual Life in Biologically Active Water

Groups of 5 cups of water containing mosquito-larva-rearing food were treated with the same dosage of the test compound. One of the 5 cups was infested just prior to treatment with about 20 first- and third-stage *Aedes aegypti* larvae (representing nonsynchronized mosquito populations). The remaining cups were infested with similar larvae at various intervals after treatment of the water with the test compound. Pupal mortality was observed through adult emergence. The test compound, the compound dosage and pupal mortality are tabulated in Table III.

TABLE II

| YELLOW FEVER MOSQUITO CONTROL | | | | | |
|---|---|---|---|---|---|
| COMPOUND | CONCENTRATION (ppm) | Larvae | Pupae | Adults | Total |
| 3,4-methylenedioxybenzyl 3,5-di-t-butyl-4-hydroxydithiobenzoate | 1.7 | 0 | 75 | 0 | 75 |
|  | 1 | 0 | 75 | 0 | 75 |
|  | 1 | 0 | 70 | 0 | 70 |
| benzyl 3,5-di-t-butyl-4-hydroxythiolobenzoate | 0.3 | 0 | 80 | 0 | 80 |
|  | 0.1 | 0 | 55 | 0 | 55 |
| benzyl 3,5-di-t-butyl-4-hydroxydithiobenzoate | 1.7 | 10 | 70 | 0 | 80 |
|  | 1 | 0 | 70 | 0 | 70 |
| benzyl 3,5-di-t-butyl-4-hydroxybenzoate | 1.7 | 0 | 10 | 0 | 10 |
| p-chlorobenzyl 3,5-di-t-butyl-4-hydroxydithiobenzoate | 1.7 | 0 | 20 | 0 | 20 |
| p-chlorobenzyl 3,5-di-t-butyl-4-hydroxythiolobenzoate | 1.7 | 0 | 40 | 0 | 40 |
| p-methoxybenzyl 3,5-di-t-butyl-4-hydroxydithiobenzoate | 1.7 | 0 | 20 | 0 | 20 |
| m-fluorobenzyl 3,5-di-t-butyl-4-hydroxydithiobenzoate | 1.7 | 0 | 50 | 0 | 50 |
| o-fluorobenzyl 3,5-di-t-butyl-4-hydroxydithiobenzoate | 1.7 | 0 | 35 | 0 | 35 |

TABLE II-continued

YELLOW FEVER MOSQUITO CONTROL

| COMPOUND | CONCEN-TRATION (ppm) | % MORTALITY Larvae | Pupae | Adults | Total |
|---|---|---|---|---|---|
| p-fluorobenzyl 3,5-di-t-butyl-4-hydroxydithiobenzoate | 1.7 | 0 | 55 | 0 | 55 |
| p-ethylbenzyl 3,5-di-t-butyl-4-hydroxydithiobenzoate | 1.7 | 0 | 10 | 0 | 10 |
| methyl 3,5-di-t-butyl-4-hydroxydithiobenzoate | 1.7 | 0 | 50 | 0 | 50 |
| methyl 3,5-di-t-butyl-4-hydroxythiolobenzoate | 1.7 | 0 | 10 | 0 | 10 |
|  | 1.7 | 0 | 100 | 0 | 100 |
| t-butyl 3,5-di-t-butyl-4-hydroxythiolobenzoate | 1 | 0 | 90 | 0 | 90 |
|  | 0.3 | 0 | 65 | 0 | 65 |
| allyl 3,5-di-t-butyl-4-hydroxydithiobenzoate | 1.7 | 65 | 0 | 0 | 65 |
|  | 1 | 0 | 55 | 0 | 55 |
| propargyl 3,5-di-t-butyl-4-hydroxydithiobenzoate | 1.7 | 0 | 70 | 0 | 70 |
|  | 1 | 5 | 50 | 0 | 55 |
| methoxymethyl 3,5-di-t-butyl-4-hydroxydithiobenzoate | 1.7 | 0 | 15 | 0 | 15 |
| methylthiomethyl 3,5-di-t-butyl-4-hydroxydithiobenzoate | 1.7 | 0 | 30 | 0 | 30 |
|  | 0.3 | 0 | 100 | 0 | 100 |
| 2-thiophenemethyl 3,5-di-t-butyl-4-hydroxydithiobenzoate | 0.1 | 0 | 75 | 0 | 75 |
| 2-thiophenemethyl 3,5-di-t-butyl-4-hydroxybenzoate | 1.7 | 0 | 75 | 0 | 75 |
| 2-pyridyl-N-oxide 3,5-di-t-butyl-4-hydroxythiolobenzoate | 1.7 | 0 | 15 | 0 | 15 |
| 3-pyridylmethyl 3,5-di-t-butyl-4-hydroxythiolobenzoate | 1.7 | 0 | 55 | 0 | 55 |
| 2-pyridylmethyl 3,5-di-t-butyl-4-hydroxythiolobenzoate | 1.7 | 0 | 60 | 0 | 60 |

TABLE III

| COMPOUND | CONCEN-TRATION (ppm) | DAYS POST TREATMENT GIVING 100% PUPAL MORTALITY Pupae from third larvae | Pupae from first larvae |
|---|---|---|---|
| benzyl 3,5-di-t-butyl-4-hydroxythiolobenzoate | 1 | 8 | 14 |
|  | 0.3 | 4 | 9 |
|  | 0.1 | 2 | — |
| benzyl 3,5-di-t-butyl-4-hydroxydithiobenzoate | 1.0 | 5 | 9 |
|  | 0.3 | 5 | 6 |
|  | 0.1 | 2 | — |

Example 20 — Fish Toxicity

Mosquito fish (*Carnbusia affinis*) were exposed to 10 ppm of benzyl 3,5-di-t-butylthiolobenzoate for 2 weeks. No fish kill was observed.

Example 21 — Mosquito Control with Petroleum Oil Formulations

A 1% by weight formulation of a variety of the benzoates of the invention was prepared with an oil composition having 96.1% by weight of a petroleum oil having an aromatic content of 8.4% by weight and a viscosity of 36.3 SSU at 100° F., 0.9% by weight of ethoxylated dodecyl phenol (molecular weight 526, and 6 mols ethylene oxide per mol phenol), and 3% by weight of polyisobutenyl succinic anhydride (molecular weight 950).

The oil formulations were tested for the control of *Aedes aegypti* larvae by applying a thin film of the oil formulation to a container containing 20 larvae, 170 ml of water and a small amount of larva-rearing food. A count was made after 2 days for larval and pupal mortality. The benzoate employed, the concentration and the results (average of two tests) are tabulated in Table IV.

Example 22 — Cabbage Looper Control

The compounds of the invention were tested as juvenile hormonal mimetic insecticides against cabbage looper (*Trichoplusia ni*) by the following procedure: 5 microliters of an acetone solution containing 100 micrograms of the test compound were applid topically to the entire length of the body of a late-fifth-stage cabbage looper larva. Normally 10 larvae were treated per test. The treated larvae were then fed until they pupated. The pupae were then induced until the adult emerged. The mortality of the pupae and adults was determined. The compounds tested and the total pupal and adult mortality are tabulated in Table V.

Example 23 — Alfalfa Weevil Control

The compounds of the invention were tested as juvenile hormonal mimetic insecticides against alfalfa weevils (*Hapera postica, Gyllenhal*) by the same procedure employed for cabbage looper, except that 5 micrograms of test compound were applied to last-stage alfalfa weevil larvae. The compounds tested and the total pupal and adult mortality are tabulated in Table VI.

Example 24 — Preparation of Cyclohexyl 3,5-di-t-butyl-4-hydroxythiolobenzoate Cyclohexyl 3,5-di-t-butyl-4-hydroxythiolobenzoate was prepared by reacting substantially equimolar amounts cyclohexyl mercaptan and 2,6-di-t-butyl-4-hydroxybenzoyl chloride in pyridine and dimethoxyethane by a procedure similar to that of Example 3. The product was a crystalline solid melting at 95°–97° C. Elemental analysis showed: %S, calc. 9.2, found 9.0.

TABLE IV

| COMPOUND | Oil Dosage, gal/ac. | PPM Benzoate/ part Water | % Mortality Larvae | Pupae | Total |
|---|---|---|---|---|---|
|  | 0.5 | 0.08 | 0 | 85 | 85 |

TABLE IV-continued

| COMPOUND | Oil Dosage, gal/ac. | PPM Benzoate/ part Water | % Mortality Larvae | Pupae | Total |
|---|---|---|---|---|---|
| t-butyl 3,5-di-t-butyl-4-hydroxythiolobenzoate | 0.33 | 0.05 | 0 | 78 | 78 |
|  | 0.5 | 0.08 | 0 | 70 | 70 |
| benzyl 3,5-di-t-butyl-4-hydroxythiolobenzoate | 0.33 | 0.05 | 0 | 78 | 70 |
|  | 0.5 | 0.08 | 0 | 90 | 90 |
| benzyl 3-5-di-t-butyl-4-hydroxydithiobenzoate | 0.33 | 0.05 | 0 | 30 | 30 |
|  | 0.5 | — | 10 | 0 | 10 |
| none | 0.33 | — | 10 | 2 | 12 |

TABLE V

| COMPOUND | % Mortality |
|---|---|
| 3-pyridylmethyl 3,5-di-t-butyl-4-hydroxythiolobenzoate | 20 |
| 2-pyridylmethyl 3,5-di-t-butyl-4-hydroxythiolobenzoate | 20 |
| 2-benzoxazolyl 3,5-di-t-butyl-4-hydroxythiolobenzoate | 30 |
| 2-furanyl 3,5-di-t-butyl-4-hydroxythiolobenzoate | 30 |
| α,α-dimethylbenzyl 3,5-di-t-butyl-4-hydroxydithiobenzoate* | 100 |
| 2-(4-pyridyl)ethyl 3,5-di-t-butyl-4-hydroxydithiobenzoate | 50–80 |
| 1-[1-(2-pyrrolidone)]ethyl 3,5-di-t-butyl-4-hydroxydithiobenzoate | 30 |
| α-methylbenzyl 3,5-di-t-butyl-4-hydroxydithiobenzoate | 100 |
| 2,6-dichlorobenzyl 3,5-di-t-butyl-4-hydroxythiolobenzoate | |

*1 microgram of test comound

TABLE VI

| COMPOUND | % Mortality |
|---|---|
| 2-pyridylmethyl 3,5-di-t-butyl-4-hydroxydithiobenzoate | 10 |
| 3-pyridylmethyl 3,5-di-t-butyl-4-hydroxythiolobenzoate | 10 |
| t-butyl 3,5-di-t-butyl-4-hydroxydithiobenzoate | 20 |
| 1-[1-(2-pyrrolidone)]ethyl 3,5-di-t-butyl-4-hydroxydithiobenzoate | 10 |
| 3,5-di-t-butyl-4-hydroxythiolobenzoic acid | 50 |

What is claimed is:

1. A method for killing mosquitos which comprises contacting pre-adult mosquitos with a metamorphosis inhibiting amount of a compound represented by the formula

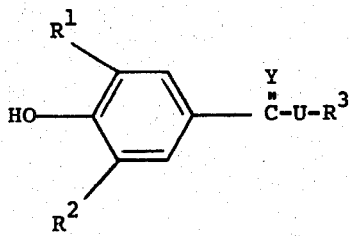

wherein Y is sulfur or oxygen, U is sulfur or oxygen, $R^1$ and $R^2$ are branched alkyl groups of 3 to 6 carbon atoms attached to the aromatic ring through a secondary or tertiary carbon atom, $R^3$ is (1) alkyl of 1 to 6 carbon atoms, (2) cycloalkyl of 3 to 10 carbon atoms, (3) 2-alkenyl of 3 to 6 carbon atoms, (4) 2-alkynyl of 3 to 6 carbon atoms, (5) alkoxyalkyl of 2 to 6 carbon atoms, (6) alkylthioalkyl of 2 to 6 carbon atoms, (7) phenylalkyl of 7 to 10 carbon atoms, or (8) phenylalkyl of 7 to 10 carbon atoms and substituted on the phenyl ring with 1 to 2 substituents selected from alkyl of 1 to 4 carbon atoms, alkoxy of 1 to 4 carbon atoms, fluorine, chlorine, or bromine.

2. The method of claim 1 wherein $R^3$ is alkyl of 1 to 3 carbon atoms.

3. The method of claim 1 wherein $R^3$ is phenylalkyl or phenylalkyl substituted on the phenyl ring with 1 to 2 substituents selected from alkyl of 1 to 4 carbon atoms, alkoxy of 1 to 4 carbon atoms, fluorine, chlorine, or bromine.

4. The method of claim 2 wherein U is sulfur.

5. The method of claim 4 wherein $R^1$ and $R^2$ are t-butyl, and $R^3$ is methyl.

6. The method of claim 3 wherein U is sulfur.

7. The method of claim 6 wherein $R^1$ and $R^2$ are t-butyl.

8. The method of claim 1 wherein $R^3$ is cycloalkyl of 5 to 8 carbon atoms and U is sulfur.

9. The method of claim 8 wherein $R^1$ and $R^2$ are t-butyl, $R^3$ is cyclohexyl and Y is oxygen.

10. The method of claim 1 wherein $R^3$ is alkoxyalkyl and U is sulfur.

11. The method of claim 10 wherein $R^1$ and $R^2$ are t-butyl, $R^3$ is methoxymethyl and Y is sulfur.

12. The method of claim 1 wherein $R^3$ is alkylthioalkyl and U is sulfur.

13. The method of claim 12 wherein $R^1$ and $R^2$ are t-butyl, $R^3$ is methylthiomethyl and Y is sulfur.

* * * * *